US00PP18843P2

(12) United States Plant Patent
Van Zanten

(10) Patent No.: US PP18,843 P2
(45) Date of Patent: May 27, 2008

(54) ***OSTEOSPERMUM* PLANT NAMED 'GG DEL MAG06'**

(50) Latin Name: *Osteospermum ecklonis*
Varietal Denomination: GG DEL MAG06

(75) Inventor: Leo Van Zanten, Oxnard, CA (US)

(73) Assignee: G + G Breeding Corporation, Oxnard, CA (US)

( * ) Notice: Subject to any disclaimer, the term of this patent is extended or adjusted under 35 U.S.C. 154(b) by 158 days.

(21) Appl. No.: 11/394,714

(22) Filed: Mar. 31, 2006

(51) Int. Cl.
*A01H 5/00* (2006.01)

(52) U.S. Cl. ..... Plt./360
(58) Field of Classification Search ..... Plt./360
See application file for complete search history.

*Primary Examiner*—Annette H Para

(57) ABSTRACT

A new and distinct *Osteospermum* plant cultivar is disclosed, characterized by large daisy type inflorescences, freely flowering under outdoor growing conditions with continuous blooming from spring through autumn, dark red-purple ray florets, and disc florets with dark blue at very center with light blue and light purple at the edges.

1 Drawing Sheet

Latin name of the genus and species: *Osteospermum ecklonis.*
Variety denomination: 'GG DEL MAG06'.

BACKGROUND OF THE INVENTION

The new cultivar 'GG DEL MAG06' is a product of open pollination in a heterogeneous population of *Osteospermum* mass selection. The new cultivar was discovered and selected by Leo Van Zanten in May 2004 in Carpinteria, Calif.

Asexual reproduction of the new cultivar 'GG DEL MAG06' by cuttings from adventitious shoots was performed in Oxnard, Calif., and has shown that the unique features of this new cultivar are stable and reproduced true to type on successive generations.

SUMMARY OF THE INVENTION

The cultivar 'GG DEL MAG06' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GG DEL MAG06.' These characteristics in combination distinguish 'GG DEL MAG06' as a new and distinct *Osteospermum* cultivar:

1. Large daisy type inflorescence;
2. Dark red purple ray florets;
3. Disc florets with dark blue at very center with light blue and light purple at edges; and
4. A free branching habit.

There is no parent variety to compare to 'GG DEL MAG06.'

In comparison to the commercially available variety 'Iringa' (U.S. Plant Pat. No. 15,632), 'GG DEL MAG06' is smaller in both height and plant spread with a wider internode length. Additionally, the new variety 'GG DEL MAG06' has more green foliage compared to the yellow-green foliage of the comparable variety. Further, the new variety 'GG DEL MAG06' has less inflorescence per plant and lighter purple ray florets. Finally, 'GG DEL MAG06' has dark blue disc florets compared to the dark purple disc florets of the comparable variety and 'GG DEL MAG06' has a wider disc diameter.

BRIEF DESCRIPTION OF THE PHOTOGRAPH

The accompanying photograph in FIG. 1 illustrates in full color a typical plant of 'GG DEL MAG06' grown in a 6-inch pot, planted late October and grown outdoors. The growing temperatures ranged from 12° C. to 15° C. at night to 12° C. to 20° C. during the day. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'GG DEL MAG06' plants grown in Oxnard, Ventura County, Calif., during the months of October through February. The growing temperature ranged from 12° C. to 15° C. at night to 12° C. to 20° C. during the day. Measurements and numerical values represent averages of typical flowering types.

Botanical classification: *Osteospermum ecklonis* cultivar 'GG DEL MAG06.'
Commercial classification: Garden-type *Osteospermum.*

PROPAGATION

Time to rooting: 10 to 14 days at approximately 21° C.
Root description: Fine, fibrous.

PLANT

Growth habit: Mounding outwardly spreading herbaceous perennial.
Height: Approximately 18 cm.
Plant spread: Approximately 30 cm.
Growth rate: Vigorous.
Branching characteristics: Free Branching.
Length of lateral branches: Approximately 12 cm.
Number of leaves per lateral branch: Approximately 42.
Age of plant described: Approximately 126 days.

FOLIAGE

Leaf:
*Arrangement.*—Alternate single.
*Average length.*—Approximately 3.1 cm.
*Average width.*—Approximately 2.1 cm.
*Shade of blade.*—Obovate.
*Apex.*—Abruptly acuminate.
*Base.*—Attenuate.
*Attachment.*—Stalked.
*Margin.*—Entire with occasional tiny serrations.
*Texture of top surface.*—Lightly pubescent.
*Texture of bottom surface.*—Lightly pubescent.
*Leaf internode length.*—Approximately 2 cm.
*Color.*—Young foliage upper side: Near Green 139A. Young foliage under side: Near Green 137A. Mature foliage upper side: Near Green 137A. Mature foliage under side: Near Green 137B.
*Venation.*—Type: Pinnate. Venation color upper side: Near Green 143C. Venation color under side: Near Green 143C.

Petiole:
*Average length.*—Approximately 1.5 cm.
*Color.*—Near Green 143C.
*Diameter.*—Approximately 0.2 cm.

BLOOM

Inflorescence:
*Flowering habit.*—Freely flowering under outdoor growing conditions with continuous blooming from spring through autumn and year round in a greenhouse environment.
*Inflorescence form.*—Daisy.
*Natural flowering season.*—Continuous throughout February to September in temperate regions.
*Number of inflorescences per lateral branch.*—Approximately 8.
*Inflorescence diameter.*—Approximately 6.2 cm.
*Inflorescence depth.*—Approximately 1.2 cm.
*Disc diameter.*—Approximately 1.45 cm.
*Inflorescence longevity on plant.*—Approximately 5 to 10 days; longevity of individual flowers are very dependent on temperature and light conditions.
*Persistence.*—Persistent.

Ray florets:
*Appearance.*—Matte.
*Texture.*—Smooth.
*Average number of ray florets per inflorescence.*—20.
*Shape.*—Oblanceolate.
*Aspect.*—Slightly cupped, facing upward or outward.
*Margin.*—Entire.
*Apex.*—Obtuse.
*Length.*—Approximately 3 cm.
*Width.*—Approximately 0.8 cm.
*Color.*—Upper surface at first opening: Near Purple 79A. Upper surface at maturity: Near Red-Purple 72A. Upper surface at fading: Near Purple 77B. Under surface at first opening: Near Purple 79C. Under surface at maturity: Near Purple-Violet 82C with longitudinal stripes of Purple 79B. Under surface at fading: Near Violet 84D with longitudinal stripes of Purple 79B.

Disc florets:
*Appearance.*—Shiny.
*Texture.*—Smooth.
*Average number of florets per disc.*—Approximately 93.
*Shape.*—Tubular.
*Apex.*—Five-pointed.
*Average length.*—Approximately 0.5 cm.
*Average width.*—Approximately 0.1 cm.
*Color.*—At first opening: Near Purple 79A. At maturity: Near Blue 103A at very center with Violet-Blue 92B at edges. At fading: Near Blue 103A at very center with Violet-Blue 92B at edges.

Peduncle:
*Length.*—Between 9 and 12 cm.
*Angle.*—Terminal peduncles, erect; secondary and tertiary peduncles, about 45° from vertical.
*Strength.*—Moderate.
*Color.*—Near Greyed-Purple 187A.
*Habit.*—Upright.
*Diameter.*—Approximately 0.2 cm.
*Surface texture.*—Lightly pubescent.

Inflorescence bud:
*Length.*—Approximately 2 cm.
*Diameter.*—Approximately 0.5 cm.
*Form.*—Elliptic.
*Color.*—Near Green 138A.

Involucral bracts (phyllaries):
*Appearance.*—Matte.
*Texture.*—Lightly pubescent.
*Number.*—Approximately 16.
*Shape.*—Lanceolate.
*Margin.*—Entire.
*Apex.*—Narrowly acute.
*Length.*—Approximately 1.9 cm.
*Width.*—Approximately 0.1 cm.
*Color.*—Upper side: Near Green 137A. Under side: Near Green 138A.

REPRODUCTIVE ORGANS

Androecium: Present on disc florets only.
*Number of stamens.*—5.
*Anther shape.*—Linear.
*Anther length.*—Approximately 1.5 mm.
*Anther color.*—Near Purple 79A.
*Amount of pollen.*—Abundant.
*Pollen color.*—Near Yellow 13A.

Gynoecium: Present on ray and disc florets.
*Pistil number.*—One.
*Pistil length.*—Approximately 6 mm.
*Stigma shape.*—Two parted.
*Stigma length.*—Approximately 1.2 mm.
*Stigma color.*—Near Purple 79A.
*Style length.*—Approximately 0.2 cm.
*Style color.*—Near Purple 76B.

OTHER CHARACTERISTICS

Disease resistance: Neither resistance nor susceptibility to diseases or pests has been observed in this variety.

Drought tolerance/cold tolerance: Plants are moderately drought tolerant. Plants need cold, less than 12.8° C. for flower induction.

Fruit/seed production: Commercially, this plant is not used or observed in a stage where seeds would be produced. Therefore, seed production has not been observed.

What is claimed is:

1. A new and distinct cultivar of *Osteospermum* plant named 'GG DEL MAG06' as herein illustrated and described.

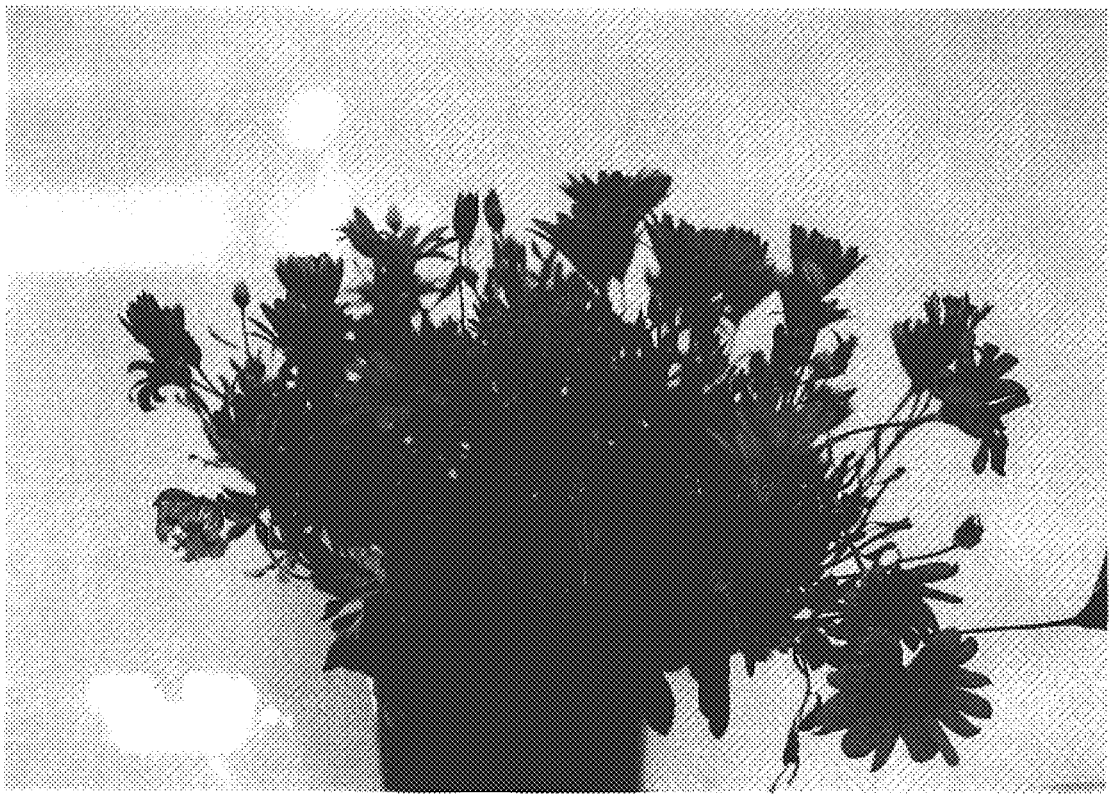

* * * * *